United States Patent [19]

Fukumoto et al.

[11] Patent Number: 4,600,888
[45] Date of Patent: Jul. 15, 1986

[54] DEVICE FOR CONTINUOUSLY MONITORING THE DENSITY OF ATMOSPHERIC SODIUM IONS

[75] Inventors: Takaaki Fukumoto; Masaharu Hama; Shinpei Kayano, all of Hyogo, Japan

[73] Assignee: Mitsubishi Denki Kabushiki Kaisha, Tokyo, Japan

[21] Appl. No.: 587,788

[22] Filed: Mar. 9, 1984

[30] Foreign Application Priority Data

May 20, 1983 [JP] Japan .................. 58-89522

[51] Int. Cl.⁴ .............. G01N 27/08; G01N 27/28
[52] U.S. Cl. ............................. 324/439; 73/28; 73/863.21; 204/409
[58] Field of Search .............. 73/170 R, 32 R, 863.21, 73/864.33, 61 R, 28; 204/1 A, 409; 324/65 R, 439, 450; 55/270; 422/88, 90

[56] References Cited

U.S. PATENT DOCUMENTS

| | | | |
|---|---|---|---|
| 2,758,079 | 8/1956 | Eckfeldt | 324/439 |
| 3,267,361 | 8/1966 | Maddox | 324/439 |
| 3,493,857 | 2/1970 | Silverman | 324/65 R |
| 3,751,967 | 8/1973 | Fick et al. | 73/863.21 |
| 4,083,766 | 4/1978 | Landon et al. | 324/439 |

FOREIGN PATENT DOCUMENTS 2938545  4/1981  Fed. Rep. of Germany .

*Primary Examiner*—Stewart J. Levy
*Assistant Examiner*—John E. Chapman, Jr.
*Attorney, Agent, or Firm*—Sughrue, Mion, Zinn, Macpeak & Seas

[57] ABSTRACT

A device for continuously monitoring variations of the density of sodium ions borne by atmospheric air. A water tank is provided having a fixed volume with a top thereof opened to the atmosphere. Pure water, having a resistivity of at least 15 M$\Omega$·cm is continuously supplied into the tank and extracted therefrom at the same rate. The conductivity or resistivity of the extracted water is measured to determine the sodium ion concentration in the air. For small densities, a sodium ion electrode meter can be employed for measuring the sodium ion density.

4 Claims, 1 Drawing Figure

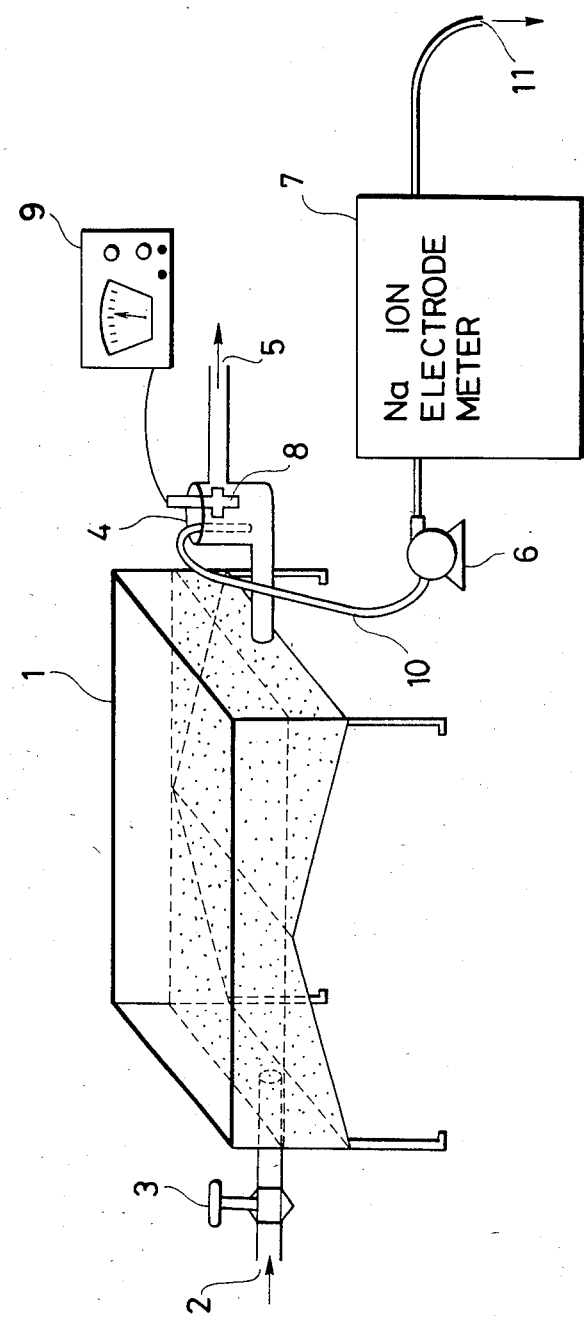

DEVICE FOR CONTINUOUSLY MONITORING THE DENSITY OF ATMOSPHERIC SODIUM IONS

BACKGROUND OF THE INVENTION

The present invention relates to a device for continuously monitoring variations of the density of sodium ions in the atmosphere.

No device for continuously monitoring nonperiodic variations of the density of sodium ions in the atmosphere has yet been known. However, methods for discontinuously detecting the density of sodium ions are well known. According to one of these methods, a predetermined amount of the air to be tested is bubbled through distilled or otherwise pure water, and the resultant solution is analyzed with an analyzing device such as an atomic absorption spectrophotometer. In accordance with another method, sea salt particles floating in the air are collected on a filter by operating a low volume sampler for a predetermined period of time. The particles are then dissolved in a predetermined amount of pure water and the water subjected to atomic absorption analysis.

However, these conventional methods are disadvantageous in that the specimen cannot be uniformly sampled. Since it is necessary to bring a specimen to an analyzing room, it is impossible to quickly measure and record the density of sodium ions or to quickly operate an alarm device.

In view of the foregoing, an object of the invention is to provide a device for continuously monitoring the density of sodium ions in the atmosphere which operates continuously and quickly.

SUMMARY OF THE INVENTION

The foregoing object and other objects of the invention have been achieved by the provision of a device for continuously monitoring the density of sodium ions in the atmosphere, which device includes a water tank having a top opened to the atmosphere, and water supplying and discharging means for causing pure water to flow into the water tank at a predetermined flow rate. Sodium ions in the atmosphere are continuously dissolved in the pure water, and the conductivity or specific resistance of the water in the tank is measured to monitor the density of sodium ions in the atmosphere.

BRIEF DESCRIPTION OF THE DRAWINGS

The single drawing FIGURE is an explanatory diagram showing the arrangement of a preferred embodiment of a device for continuously monitoring the density of sodium ions in the atmosphere.

DESCRIPTION OF THE PREFERRED EMBODIMENTS

The single FIGURE in the accompanying drawing shows the arrangement of a device for continuously monitoring the density of sodium ions in the atmosphere constructed according to the invention. In the FIGURE, reference numeral 1 designates a water tank which is opened at the top so that the surface of the water therein is in contact with atmospheric air. Pure water having a resistivity of 15 MΩ·cm or higher is supplied through a water supplying pipe 2 into the water tank at a flow rate set by a valve 3. Water is discharged from the tank 1 to a water sampling tank 4 through a water discharging pipe 5 at a rate of, for instance, 0.01 m$^3$/hr. Water from the tank 4 is supplied to a sodium ion electrode meter 7 by a pump 6 at a rate so that the level of the water in the tank 1 is maintained unchanged.

While pure water is being supplied into the tank 1 at a predetermined flow rate as described above, sea salt particles in the air are dissolved to form ions in the water. Variations of the pure water's resistivity due to the presence of such ions is continuously measured to monitor the density of salt in the air. In the case where the density of salt in the air is 100 $\mu$g/m$^3$ or more, an ohmmeter 9 having a probe 8 inserted into the discharged water sampling tank 4 is employed to measure the resistivity of the water. Such an instrument has a typical response time of 10 to 30 seconds in a range of 100 KΩ·cm to 1 MΩ·cm. Instead of an ohmmeter, an instrument for measuring conductivity may be used.

In the case when the density of salt in the atmosphere is small, for instance, less than 100 $\mu$g/cm$^3$, the resistivity of the water is decreased more by dissolution of carbon dioxide gas from the air than by sodium ions. In this case, a sodium ion electrode meter 7 is used. More specifically, the pump 6 is operated to supply water from the discharged water sampling tank 4 through a Teflon TM tube 10 to the detecting section of the sodium ion electrode meter 7 at a flow rate of about 0.1 m$^3$/hr. The discharged water which has been analyzed by the meter 7 is discharged through a water discharge pipe 11. The sodium ion electrode meter 7 is capable of measuring densities of the order of 1 to 10,000 ppb, thus monitoring the density of salt in the air as the density of sodium ions. The sodium ion electrode meter 7 is effective in separating the sodium ions from other interfering ions, especially from common air-borne pollutants such as $SO_2$ and $NO_x$.

The speed of response of the sodium ion electrode meter 7 is relatively slow, typically two or three minutes. However, this drawback is overcome when the ohmmeter 9 is used. That is, when the density of salt in the air is above a certain level, the ohmmeter 9 having a high speed of response is activated. If desired, an alarm device (not shown) can operate to issue a warning when the output of the ohmmeter exceeds a predetermined value.

In order to increase the sensitivity of detection, it is desirable that the area of the opening of the water tank 1 be large so that the contact area of the water with the air is large. In this connection, in order to maintain a steady condition of the water surface, the bottom of the water tank is raised at the middle, away from the water supplying pipe and the water discharging pipe.

As is apparent from the above description, according to the invention, pure water is continuously supplied into a water tank opened to the air, and means for measuring the conductivity or resistivity of the water is arranged in the water discharging pipe. With this arrangement sodium ions in the air are dissolved in the pure water, and the density of the sodium ions is monitored by monitoring the conductivity or resistivity of the water with an instrument having a high response speed. As the sodium ion electrode meter is used in combination with an ohmmeter or the like, the effects of other ion materials are eliminated, and therefore even when the density of sodium ions is small, it can be monitored satisfactorily.

We claim:

1. A device for continuously monitoring the density of air-borne sodium ions, comprising:

a water tank having a predetermined volume and having a top opened to the atmosphere;

water supplying and discharging means for continuously supplying pure water having a resistivity of at least 15 M$\Omega$·cm to said water tank at a predetermined flow rate and for continuously discharging said pure water from said water tank at said predetermined flow rate so that the level of said pure water in said water tank is maintained unchanged; and means for measuring the density of sodium ions in said pure water by continuously measuring a conductivity or resistivity of said pure water, said measuring means being arranged in a water discharging pipe coupled to said supplying and discharging means.

2. A device for continuously monitoring a density of sodium ions in the atmosphere, comprising:

a water tank having a predetermined volume and having a top opened to the atmosphere;

water supplying and discharging means for continuously supplying pure water having a resistivity of at least 15 M$\Omega$·cm to said water tank at a predetermined flow rate and for continuously discharging said pure water from said water tank at said predetermined flow rate so that the level of said pure water in said water tank is maintained unchanged;

means for continuously measuring a conductivity or resistivity of said pure water, said measuring means being arranged in a water discharging pipe coupled to said supplying and discharging means; and a sodium ion electrode meter for measuring a density of sodium ions in said pure water received through said water discharging pipe.

3. The device of claim 2, wherein said water tank tapers from a center portion thereof to a side portion thereof to which said water discharging pipe is coupled.

4. The device of claim 2, wherein said means for continuously measuring said conductivity or resistivity is employed for a sodium ion density of 100 $\mu$g/m$^3$ or more, and said sodium ion electrode meter is employed for a sodium ion density below 100 $\mu$g/$^3$.

* * * * *